(12) United States Patent
Emperaire

(10) Patent No.: US 6,407,057 B1
(45) Date of Patent: *Jun. 18, 2002

(54) OVULATION TRIGGERING DRUGS

(75) Inventor: Jean-Claude Emperaire, Bordeaux (FR)

(73) Assignee: Applied Research System ARS Holding N.V., Curacao (AN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,560

(22) PCT Filed: Jan. 31, 1997

(86) PCT No.: PCT/FR97/00198

§ 371 Date: Dec. 9, 1997

§ 102(e) Date: Dec. 9, 1997

(87) PCT Pub. No.: WO97/27868

PCT Pub. Date: Aug. 7, 1997

(30) Foreign Application Priority Data

Feb. 2, 1996 (FR) ............................................. 96 01303

(51) Int. Cl.⁷ .............................................. A61K 38/24

(52) U.S. Cl. .............................. 514/2; 514/21; 424/455; 424/457; 424/458; 424/459; 424/489; 424/490; 424/497

(58) Field of Search ....................... 514/2, 21; 424/457, 424/455, 458, 459, 489, 490, 497

(56) References Cited

U.S. PATENT DOCUMENTS

| | | | |
|---|---|---|---|
| 4,997,816 A | | 3/1991 | Hyland et al. ................. 514/12 |
| 5,304,377 A | * | 4/1994 | Yamada et al. .............. 424/426 |
| 5,480,656 A | * | 1/1996 | Okada et al. ................ 424/493 |

FOREIGN PATENT DOCUMENTS

| | | |
|---|---|---|
| EP | 0 119 168 | 9/1984 |
| EP | 0 193 277 | 9/1986 |
| FR | 2 581 544 | 11/1986 |
| WO | 93/13799 | 7/1993 |

* cited by examiner

Primary Examiner—Jean C. Witz
(74) Attorney, Agent, or Firm—Foley & Lardner

(57) ABSTRACT

The invention relates to medicaments for initiating ovulation comprising LH in an administrable form which ensures an increase in LH plasma levels for a period of some 40 to 60 hours.

7 Claims, No Drawings

OVULATION TRIGGERING DRUGS

The invention relates to medicaments for initiating ovulation.

It is known that ovulation is initiated physiologically by the release of LH, which takes place in the middle of the menstrual cycle and causes ovulation from ripe follicles; a release of FSH of smaller magnitude takes place simultaneously, probably acting synergistically with LH.

In treatment, it is preferable to provoke the initiation of ovulation for reasons of efficiency and programming even though spontaneous initiation of ovulation is always possible.

Chorionic gonadotropic hormone, or HCG, which extracted from the urine of pregnant women and has biological activity of the LH type, has been very widely used for this purpose since the 1930s.

Since then the initiation of ovulation during menstrual cycles stimulated by anti-oestrogens or HNG has been brought about by a single injection of 5000 or 10000 I.U. of HCG.

HCG nevertheless has its own specificity with respect to LH, giving rise to reactions which differ according to the receptors, and which give it a prolonged half-life in comparison with LH.

HCG has the advantage of being effective in initiating ovulation and having a low production cost.

But it has very major potential disadvantages. Apart from the need to have sufficient collected urine to extract marketable quantities of HCG, two major risks may arise, namely an ovarian hyperstimulation effect, which might occur to a greater or lesser extent when HCG is administered with exaggerated follicular stimulation, and multiple pregnancies, which are a coroliary of the complication. These two disadvantages significantly mar the use of HCG in treatment, and make it desirable to use LH for initiating ovulation.

The use of indigenous LH has been envisaged. With a few very rare exception, patients receiving ovulatory stimulation have a reserve of LH in the pituitary which can be mobilized through the use of GuRH itself, or one of its commercially available agonists. The administration of an agonist gives rise to a very major release of LH, which is wholly comparable with the pre-ovulatory physiological peak, but this release rarely lasts longer than 24 hours, whereas the physiological peak extends over about 48 hours.

This way of initiating ovulation with endogenous LH virtually eliminates the risk of ovarian hyperstimulation, as a result of the weaker biological activity of LH and its shorter half life in comparison with HCG. Its dilution half-life is in fact about 1 hours, and its elimination half life is about 24 hours, that is ten times shorter than that of HCG. Likewise it would seem that the risk of multiple pregnancies is smaller when this method is used.

Finally, the administration of a GnRH agonist also mobilises pituitary FSH synchronously with the release of LH, thus reproducing the physiological peak more faithfully.

However, the shortness of the period during which LH is released is this way is not appropriate for initiating ovulation in a number of woman. Every woman has in fact a specific LH peak profile and in general an increase in LH for more than 24 hours is necessary to initiate ovulation under satisfactory conditions. It follows that the initiation of ovulation by endogenous LH mobilized by a GnRH agonist can depend on a luteal phase of satisfactory quality, with satisfactory chances for conception, but also, a short luteal phase (lasting 8 days of less) or an inadequate luteal phase (of normal length but with progesteronaemia below 8 ng/ml).

In order to overcome these disadvantages it has been suggested that exogenous LH obtained from the human pituitary should be used. However, for obvious reasons of availability, it has not been possible to continue experiments with such a material for a long time. Obtaining LH in recombinant from has made it possible to continue with this type of experimentation, but given the half life of LH the initiation of ovulation by recombinant LH means that large doses have to be injected. Smaller doses are likely to give rise to a relatively brief LH plasma peak in comparison with the physiological peak, and are likely to give rise to the same problems as with enodgenous LH.

Injections then have to be repeated, which gives rise to the dual problem of acceptability by the patient and cost, as the production cost of recombinant LH is high.

The inventor's work in this field has demonstrated that the problems mentioned above can be overcome by administering LH in the form of a medicament which brings about a release which reproduces the physiological peak of approximately 48 hours more faithfully.

The invention therefore relates to the provision of new forms for the administration of medicaments based on LH for initiating ovulation.

Medicaments for the initiation of ovulation according to invention are characterised in that they incorporate LH in an administrable form which ensures an increase in the plasma level of LH for approximately 40 to 60 hours.

The use of LH in such an administrable form gives rise to a satisfactory ovulation process.

Advantageously the LH may be used in association with FSH, by which means the physiological process can be reproduced more faithfully and the quantity of LH required to initiate ovulation can undoubtedly be reduced.

Appropriate proportions correspond to a LH to FSH ratio of approximately 5.

Endogenous forms of these hormones or their a β sub-units, or again recombinant forms of these hormones or their sub-units, such as are produced by genetic engineering, are used. It is also possible to use therapeutic analogues of LH of FSH, or peptide or non-peptide LH and FSH agonists, which may act over a long period. Compounds of this type may be produced by genetic engineering, or by synthesis, and are described for example by Boime et al., in "in GnRH, GnRH analogs, gonadotropins and gonadal peptides", F. Bouchard, A. Garaty, HJT Coeningh Bennink and SN Pavlov Eds, The Parthenon Publishing Group, London 1993, p. 347–356.

The administrable forms correspond to particles having a size of approximately 1 to 250 $\mu$, see below.

In accordance with one embodiment of the invention these particles are based on a concentrate of LH and, if applicable, FSH.

Preferred particles of this type comprise lyophilisates, which may or may not be stabilized with source and/or salts of dicarboxylic acids.

In accordance with another embodiment of the invention, the particles comprise a solid envelope enclosing the LH, which may be associated with FSH and pharmaceutical excipients.

The envelope may then control the release of the active ingredient.

Appropriate materials for forming the envelope comprise biodegradable polymers. Among these polymers mention may be made of polylactic acid or a copolymer of lactic acid and glycolic acid.

In accordance with other embodiments the particles comprise a continuous matrix of the supporting material within which the active ingredient is dispersed.

These different forms are administered by injection or as a subcutaneous or intramuscular implant.

The dose of LH injected to obtain satisfactory ovulation in this form should be between approximately 10,000 and 25,000 I.U.

Toxicological investigations performed show that the medicaments according to the invention are harmless.

Other features and advantages of the invention are provided in the examples which follow:

EXAMPLE 1

Injectable preparation

Bottles containing microspheres of LH enclosing the following ingredients are prepared:

LH: 3 mg

Excipient: di-lactic-coglycolic polymer: approximately 170 mg

Mannitol: 85 mg

Sodium carboxymethylcellulose: 30 mg

Polysorbate 80: 2 mg

The following are used as a suspension medium for one ampoule:

Mannitol: 16 mg

Water for injectable preparations: q.s.p. 2 g

The lactide-glycolide copolymer is a biocompatible and biodegradable synthetic polyester such as is used in human medicine, in particular for the manufacture of absorbable surgical sutures.

Preparation of the microsphates:

The procedure described by Ogawa et al. in Chem. Pharm. Bull., 36 (3) 1095–1103, 1988, is advantageously used.

The microsphere are obtained by transferring macromolecules is a solvated state to an interphase, namely the coacervate phase. The coacervation product is then transformed into a gel containing the particles of active ingredient, and then solidified.

A dispersion of the active ingredient in lactic-glycolic copolymer solution is then added slowly and with stirring. The solubility of the copolymer is progressively reduced by adding a non-solvent. The copolymer then coacervates slowly second the suspended LH particles. The microspheres are then hardened by immersion, separated by filtration, washed, dried and analyzed to determine their LH content.

Suitable packaging is provided by adding other necessary ingredients for the preparation of an injection or a subcutaneous or intramuscular implant to the microspheres.

EXAMPLE 2

Toxicology studies

No sign of toxicity appeared for doses up to 200,000 I.U./kg tested subcutaneously and intravenously, in either single dose acute toxicity tests or chronic toxicity tests. This dose represents at least 1000 times the dose which it is intended to use in clinical practice.

Acute toxicity measurements yielded an LD50 of the order of 100 mg in rate when administered intraperitoneally. The LD50 could not be determined at doses of 200,000 times the normal therapeutic dose (mice).

Chronic toxicity investigations in rats and monkeys at doses of 2, 20, 200 μg of microparticles/kg administered subcutaneously every day over a period of 6 months showed that the effects observed were essentially related to the activity of the LH, or the LH associated with FSH.

What is claimed is:

1. A method of initiating ovulation in a mammal, comprising administering to said mammal at the middle of the menstrual cycle a dose of luteinizing hormone (LH) in a dosage between 10,000 and 25,000 I.U. so as to obtain a peak of the LH level for 40 to 60 hours in the plasma of said mammal, wherein said LH is incorporated into microparticles made of a biodegradable polymer.

2. The method according to claim 1, wherein said mammal is a human.

3. The method according to claim 1, wherein said luteinizing hormone is recombinant luteinizing hormone.

4. The method according to claim 1, wherein said biodegradable polymer is a lactide glycolide copolymer.

5. The method according to claim 1, wherein LH is administered in combination with follicle stimulating hormone.

6. The method according to claim 1, wherein said microparticles comprise a stabilizer.

7. The method according to claim 6, wherein said stabilizer is selected from the group consisting of sucrose and salts of dicarboxylic acid.

\* \* \* \* \*